United States Patent
Lu et al.

(10) Patent No.: US 10,800,689 B2
(45) Date of Patent: Oct. 13, 2020

(54) MAGNETIC NANOPARTICLE MICROBIAL COMPOSITE WITH CORE-SHELL STRUCTURE, PREPARATION METHOD THEREOF, AND ITS APPLICATION IN THE TREATMENT OF AZO DYES

(71) Applicant: SOOCHOW UNIVERSITY, Suzhou (CN)

(72) Inventors: Jianmei Lu, Suzhou (CN); Dongyun Chen, Suzhou (CN)

(73) Assignee: SOOCHOW UNIVERSITY, Suzhou (CN)

( * ) Notice: Subject to any disclaimer, the term of this patent is extended or adjusted under 35 U.S.C. 154(b) by 132 days.

(21) Appl. No.: 16/164,060

(22) Filed: Oct. 18, 2018

(65) Prior Publication Data
US 2019/0127252 A1    May 2, 2019

(30) Foreign Application Priority Data
Oct. 26, 2017   (CN) .......................... 2017 1 1023310

(51) Int. Cl.
*C02F 3/34*     (2006.01)
*C12N 11/14*    (2006.01)
*C02F 1/48*     (2006.01)
*C02F 101/30*   (2006.01)

(52) U.S. Cl.
CPC ............... *C02F 3/348* (2013.01); *C02F 1/48* (2013.01); *C12N 11/14* (2013.01); *C02F 1/488* (2013.01); *C02F 2101/308* (2013.01); *C02F 2305/08* (2013.01)

(58) Field of Classification Search
CPC .................................................. C02F 2305/08
See application file for complete search history.

(56) References Cited

PUBLICATIONS

Liu et al., Advanced Materials Research, 2013, 631-632:490-493.*
Sharma et al., Sci Rep., 2018, 8:14766 or pp. 1-11 as printed.*

* cited by examiner

*Primary Examiner* — Bin Shen
(74) *Attorney, Agent, or Firm* — SZDC Law P.C.

(57) ABSTRACT

The invention discloses a magnetic nanoparticle microbial composite material with a core-shell structure and a preparation method thereof as well as application of the magnetic nanoparticle microbial composite material in azo dye treatment. The preparation method comprises the following steps: putting ferroferric oxide into an ethanol solution with ferric trichloride and trimesic acid; carrying out layer-by-layer self-assembly and ultrasonic condition reaction in sequence to prepare modified ferroferric oxide nanoparticles; then loading the modified composite material on the surfaces of microorganisms. The composite material prepared by the preparation method disclosed by the invention has the advantages of high adsorption effects and capability of carrying out local enrichment on the dye; meanwhile, magnetic separation can be performed, and thereby the azo dye can be removed efficiently.

7 Claims, 5 Drawing Sheets

MAGNETIC NANOPARTICLE MICROBIAL COMPOSITE WITH CORE-SHELL STRUCTURE, PREPARATION METHOD THEREOF, AND ITS APPLICATION IN THE TREATMENT OF AZO DYES

This application claims priority to Chinese Patent Application No.: 201711023310.5, filed on Oct. 26, 2017, which is incorporated by reference for all purposes as if fully set forth herein.

FIELD OF THE INVENTION

The invention belongs to the field of composite material preparation, in particular to a magnetic nanoparticle microorganism composite material with a core-shell structure and a preparation method thereof, and its application in azo dye processing.

TECHNICAL BACKGROUND

With the social and economic development, environmental problems are particularly prominent, arousing strong concern. As a kind of synthetic dye, azo dyes have a wide range of applications in the fields of industry, papermaking, leather, cosmetics and foodstuffs. However, due to improper use and poor supervision, azo dyes have a great impact on people's living environment, so how to deal with azo dyes have become the research hotspot. Initially, the adsorption method as a simple and direct, the adsorption effect of significant concern, but the high cost, as well as secondary pollution and low recycling impede its development. Therefore, looking for an economical and sustainable method has become a hot topic both at home and abroad. Biodegradation has the economic, environmental and sustainable advantages aroused people's attention, if the direct use of microorganisms to degrade the dye, the degradation is a longer time, the high concentrations of dyes will also affect the microorganisms. Therefore, the simple use of microorganisms has been limited in practice.

SUMMARY OF THE INVENTION

The present invention provides a magnetic nanoparticle microorganism composite material with a core-shell structure and a preparation method for azo dye treatment, magnetic nanoparticles are modified onto microorganisms in order to achieve local dye enrichment and separation effect, achieve the effect of efficient treatment of dye wastewater.

In order to achieve the above object, the specific technical solution of the present invention is as follows:

A preparation method of magnetic nanoparticle microbial composite material with core-shell structure, comprising the following steps:

(1) dissolving a mixture of ferric chloride, sodium citrate, sodium acetate, and ethylene glycol at 180° C. to 200° C. for 8 to 10 hours to prepare ferroferric oxide nanoparticles; then dispersing the ferroferric oxide nanoparticles to the alcohol solution, and then adding thioglycolic acid ultrasonically reacting to prepare modified ferroferric oxide nanoparticles;

(2) the modified ferroferric oxide nanoparticles are sequentially reacted with ferric chloride and trimesic acid to prepare core-shell structured magnetic nanoparticles; said modified ferroferric oxide nanoparticles are sequentially reacted with ferric chloride and trimesic acid for 8 to 20 times;

(3) the core-shell structured magnetic nanoparticles are modified to the surface of microbial to prepare magnetic nanoparticle microbial composite with core-shell structure.

The present invention also disclosed a preparation method of magnetic nanoparticle microbial composite material with core-shell structure, comprising the following steps:

(1) Dissolving a mixture of ferric chloride, sodium citrate, sodium acetate, and ethylene glycol at 180° C. to 200° C. for 8 to 10 hours to prepare ferroferric oxide nanoparticles; and then dispersing the ferroferric oxide nanoparticles to the alcohol solution, then adding thioglycolic acid, ultrasonically reacting to prepare modified ferroferric oxide nanoparticles;

(2) the modified ferroferric oxide nano particles are sequentially reacted with ferric chloride and trimesic acid to prepare magnetic nanoparticles with core-shell structure; said modified ferroferric oxide nanoparticles are sequentially reacted with ferric chloride and trimesic acid for 8 to 20 times.

The present invention also disclosed a preparation method of a modified ferroferric oxide nanoparticle, characterized in comprising the following steps: reacting a mixture of ferric chloride, sodium citrate, sodium acetate, and ethylene glycol at 180° C. to 200° C. for 8 to 10 hours to prepare ferroferric oxide nanoparticles; then dispersing the ferroferric oxide nanoparticles into an alcohol solution, then adding thioglycolic acid, and ultrasonically reacting to prepare modified ferroferric oxide nanoparticles.

The above technical solutions can be exemplified as follows:

(1) After dissolving iron trichloride, sodium citrate and sodium acetate in ethylene glycol completely, stirring for 30 minutes, and then placing the mixture in a reaction vessel at 180° C. to 200° C. for 8 to 10 hours, followed by cooling, washing, to prepare ferroferric oxide nanoparticles; dispersing the prepared ferroferric oxide nanoparticles into ethanol, then adding thioglycolic acid, and reacting under ultrasonic conditions to obtain modified ferroferric oxide nanoparticles;

(2) The modified ferroferric oxide nanoparticles are placed in an ethanol solution of ferric chloride for half an hour, then separated and washed, and then reacted in a solution of trimesic acid for 1 hour. This operation step is repeated 8 to 20 times to obtain core-shell structured magnetic nanoparticles;

(3) The core-shell structured magnetic nanoparticles are modified to the surface of the microorganism to obtain a composite material.

In the above technical solution, the mass ratio of ferric chloride, sodium citrate and sodium acetate is 1:(1.5 to 2):10; The ferroferric oxide prepared by the invention is advantageous for subsequent modification, and at the same time, has a large specific surface area, which is favorable for the adsorption performance of the whole material.

In the above technical solution, the mass ratio of ferroferric oxide nanoparticles and thioglycolic acid is 100:(1 to 2); the ultrasonic reaction is carried out at room temperature, ultrasonic reaction time is 6 to 7 hours. After ultrasonic reaction, the product is washed with ultrapure water and ethanol to prepare modified ferroferric oxide nanoparticles. After modification, the surface of the nanoparticle has a carboxyl group, and the carboxyl group is an essential group for the next layer self-assembly step. Conducive to self-assembly stability and success.

In the above technical solution, the modified ferroferric oxide nanoparticles are sequentially placed in an ethanol solution of ferric chloride and trimesic acid, and after each reaction, ultrasonic treatment is performed, and after 8 to 20 times of reaction, the product is washed with ultrapure water and ethanol, and then dried to obtain core-shell structured magnetic nanoparticles. By this method, a porous nanometal organic framework can be coated on the surface of the ferroferric oxide, and the structure has strong selective adsorption capacity, and the core-shell nanoparticles can also be used for magnetic separation.

In the above technical solution, the core-shell magnetic nanoparticles are modified to the surface of the microorganism, and then the dye is adsorbed and degraded. The mass ratio of the magnetic nanoparticles to the microorganism is 1:(15 to 20), the core-shell magnetic nanoparticles are reacted with the microorganisms in a buffer solution for 12 hours, and then washed by centrifugation, followed by washing with a buffer solution to effect modification of the core-shell structured magnetic nanoparticles to the surface of the microorganism.

According to the technical solution of the present invention, the prepared magnetic core-shell nanoparticles are loaded on the surface of the microorganism to combine the adsorption and the biodegradation, and the respective advantages are fully utilized, thereby solving the disadvantages of the existing single microorganisms and the adsorption method. Therefore, the present invention further discloses the use of a magnetic nanoparticle composite material with core-shell structure in treating a dye, and discloses the above-mentioned magnetic nanoparticle with core-shell structure and the modified ferroferric oxide nanoparticle in preparing a dye treating agent, such as the treatment of dye wastewater.

ADVANTAGES OF THE INVENTION

The method disclosed by the invention of modifying the core-shell magnetic nanoparticles into microorganisms has the advantages of low economic cost, easy availability of raw materials, safe and convenient operation, magnetic separation can be carried out to improve the degradation effect, and the dye can also be partially enriched in the process, so that the dye can be degraded efficiently and the advantages of the combination of adsorption and biological methods can be effectively exerted.

DETAILED DESCRIPTION OF THE INVENTION

Embodiment 1:

A preparation method of a magnetic nanoparticle microorganism composite material with a core-shell structure comprises the following steps:

(1) After dissolving 0.1 g of ferric chloride, 0.15 to 0.2 g of sodium citrate, and 1 g of sodium acetate in 20 ml of ethylene glycol, the mixture was stirred for 30 minutes, and then the mixture was placed in a reaction vessel at 200° C. for 9 hours. Then, cooling and washing to prepare ferroferric oxide nanoparticles; dispersing prepared 10 mg of the ferroferric oxide nanoparticles into 10 ml of ethanol, then adding 0.1 to 0.2 mg of thioglycolic acid, and reacting at room temperature under ultrasonic conditions for 6 hours, the product is washed with ultrapure water and ethanol to prepare modified ferroferric oxide nanoparticles;

(2) 0.5 g modified iron tetroxide nanoparticles put into 30 ml 10 mmol per liter ferric chloride in ethanol for half an hour, then separated and washed, react in 30 ml 10 mmol per liter of trimellitic acid solution for 1 hour, this procedure was repeated 10 times to prepare core-shell magnetic nanoparticles;

(3) 100 mg core-shell magnetic nanoparticles and 1.5 to 2 g of microorganisms in phosphate buffer solution for 12 hours, the reaction was centrifuged and washed with a buffer solution, and core-shell structure of magnetic nanoparticles modified to the microbial surface, thereby preparing a magnetic nanoparticle microorganism composite having a core-shell structure.

Figure 1:
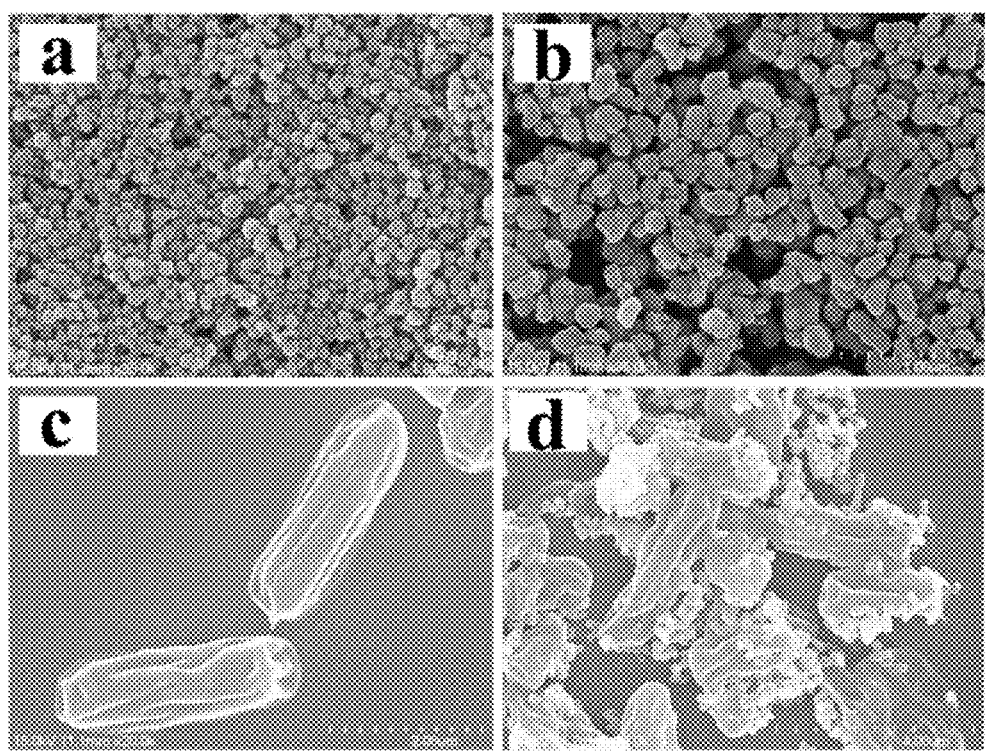
FIG. 1 is SEM image of ferroferric oxide nanoparticles, core-shell structured magnetic nanoparticles, micro-organisms, and magnetic nano-particle microbial composites with a core-shell structure.

FIG. 1 is a SEM image of ferroferric oxide nanoparticles (a), core-shell structured magnetic nanoparticles (b), microorganisms (c), and magnetic nanoparticle-based microbial composites; It can be seen from the figure that the $Fe_3O_4$ nanoparticles are spherical and uniformly distributed, at the same time, it can be seen that the surface of the modified core-shell magnetic nanoparticle becomes more rough, It's easier to load with microbes, it can be seen that the microorganisms are cylindrical, and the magnetic nanoparticles have been successfully loaded onto the surface of microorganisms, this is a crucial step toward degradation.

Figure 2:
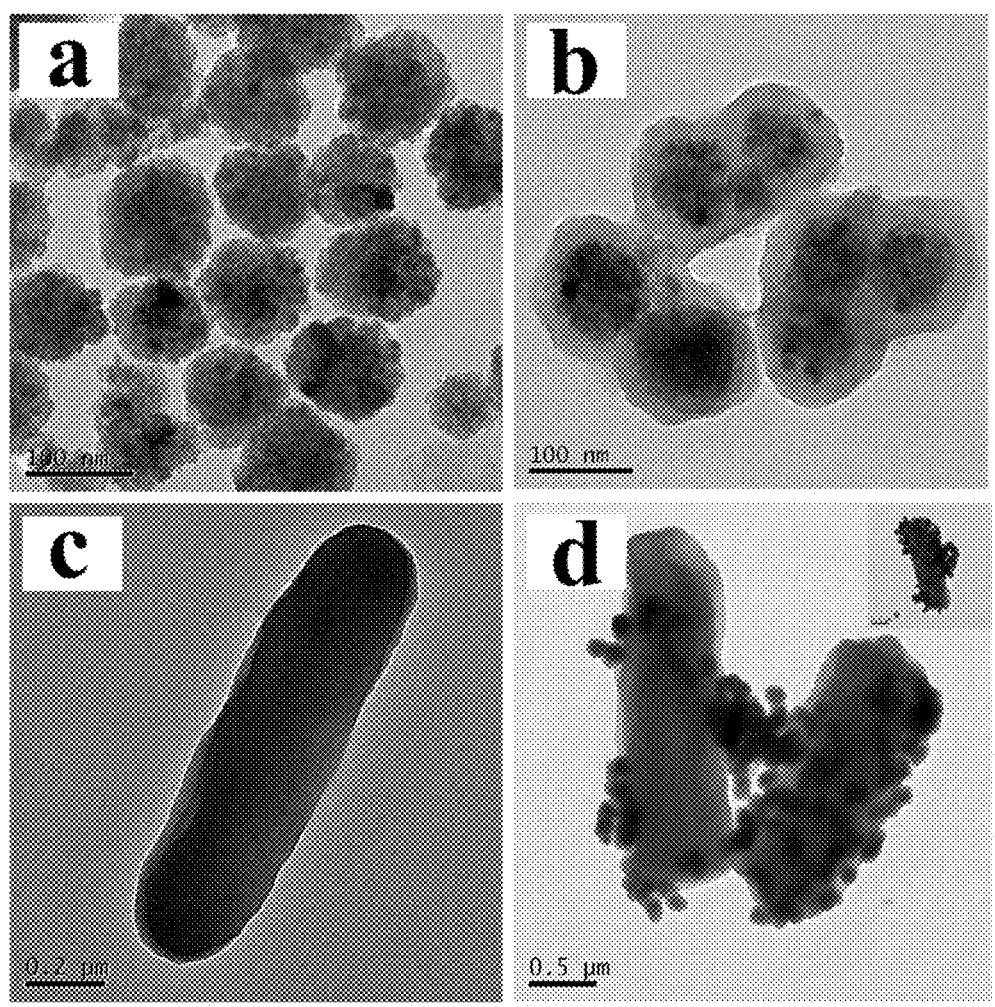
FIG. 2 is TEM image of ferroferric oxide nanoparticles, core-shell structured magnetic nanoparticles, micro-organisms, and magnetic nano-particle microbial composites with a core-shell structure.

FIG. 2 is a TEM image of the ferric oxide nanoparticles (a), the core-shell structure magnetic nanoparticles (b), the microorganisms (c), and the magnetic nanoparticle microorganism composite material (d); As can be seen from the figure, the modified ferroferric oxide nanoparticle become nucleation shell structure, this can increase its specific surface area, increase the adsorption of dyes, in the meantime, it can be seen that the composite nanoparticle of the core-shell structure has been successfully loaded onto the surface of the microorganism.

Figure 3:
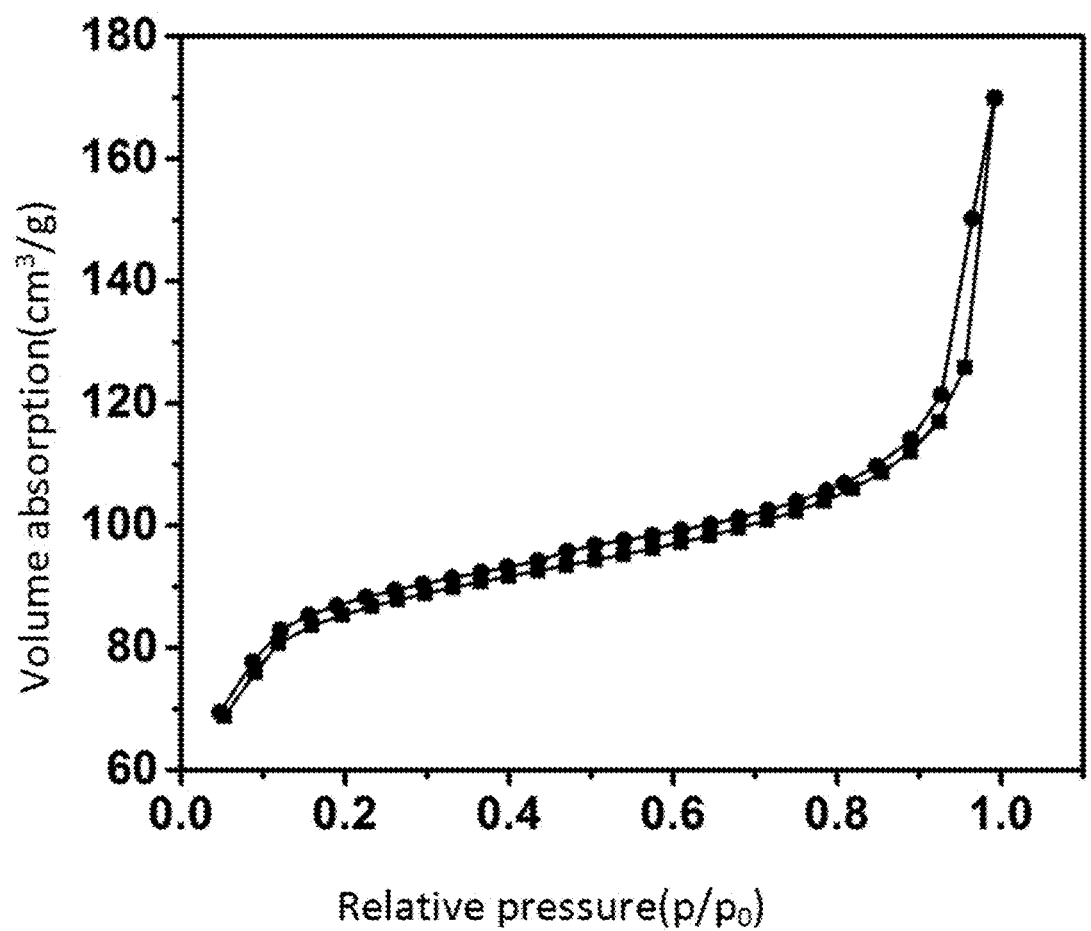
FIG. 3 is a BET diagram of core-shell magnetic nanoparticles.

FIG. 3 for the core-shell magnetic nanoparticles BET; It can be calculated from the figure, the specific surface area is 305.7 $m^2/g$, descript that composite particles have a strong adsorption capacity.

Figure 4:
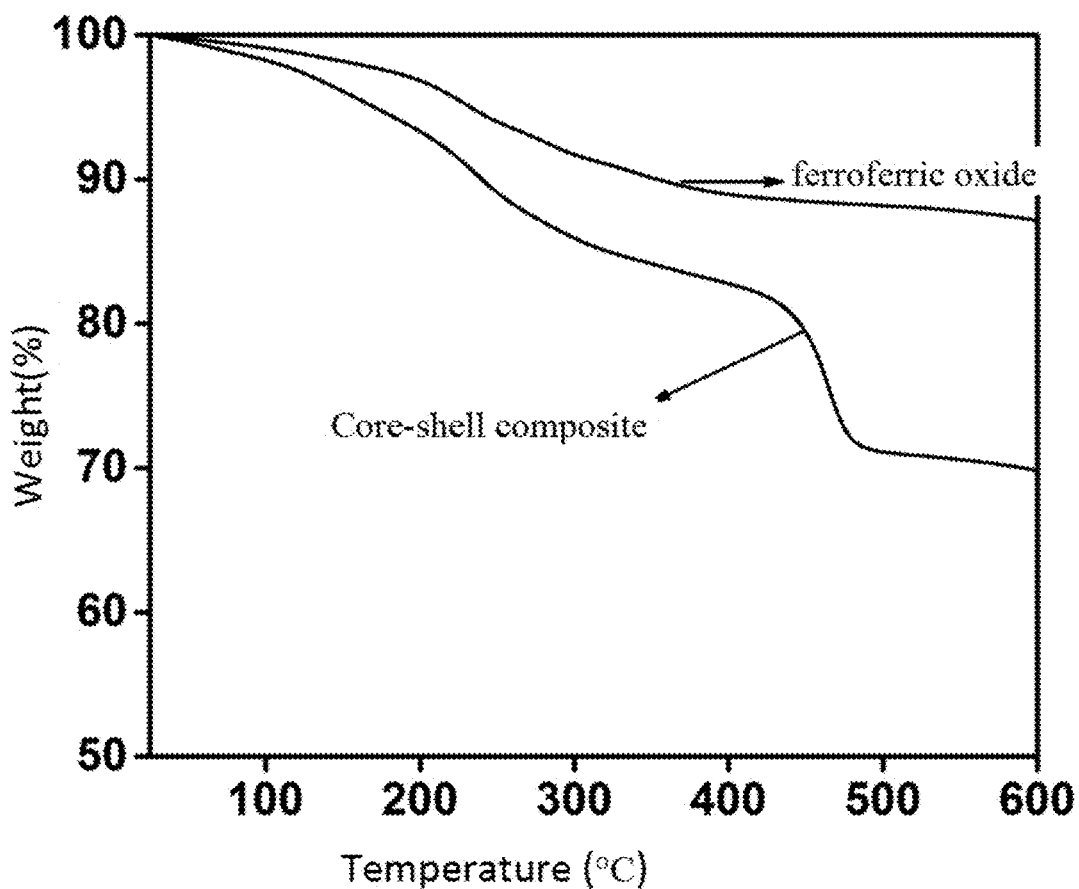
FIG. 4 is a thermogravimetric graph of core-shell magnetic nanoparticles.

FIG. 4 is a thermogravimetric diagram of core-shell magnetic nanoparticles; As can be seen from the figure, the modified material above the ferroferric oxide is about 20%, and the stability of the composite material is 400° C.

Embodiment 2:

2 g magnetic nanoparticle microorganism composite having a core-shell structure as well as free microorganisms that have been inoculated and then enriched in liquid medium were placed in 50 mL concentrations of 50 and 25 mg per liter of acidic orange solution for degradation test, after magnetic separation repeat the experiment three times to test the cycle performance.

Figure 5:
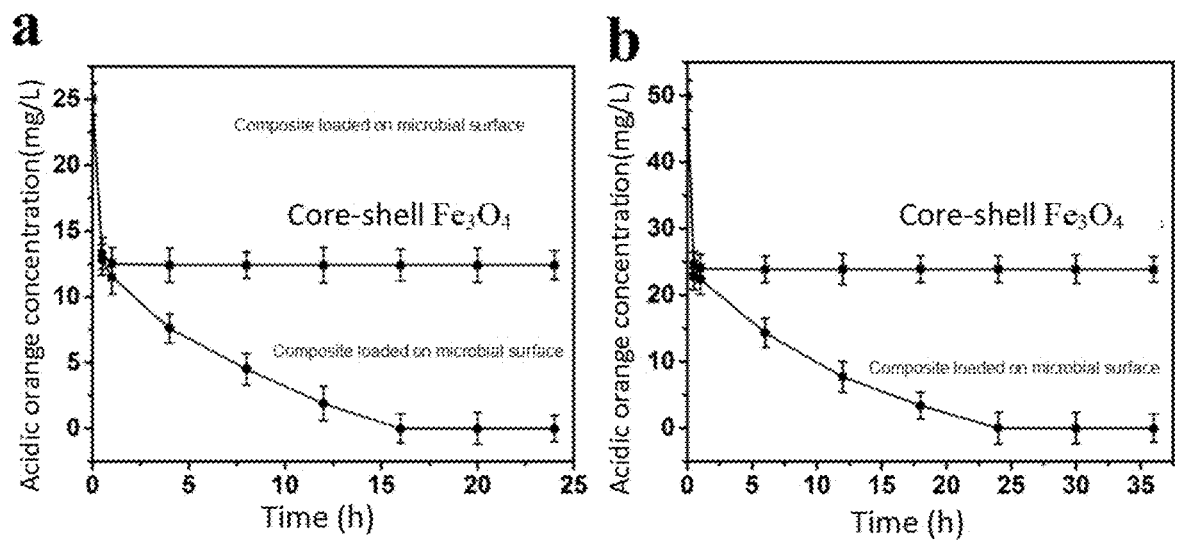
FIG. 5 is a core-shell structure of the magnetic nanoparticle microbial composite material degradation effect diagram.

FIG. 5 shows the degradation efficiency of a magnetic nanoparticle microorganism composite having a core-shell structure. It can be seen from the figure that when the initial concentrations were 25 mg per liter (a) and 50 mg per liter (b) respectively. The composite material of the present invention can complete the dye degradation in 15 hours and 25 hours.

Figure 6:
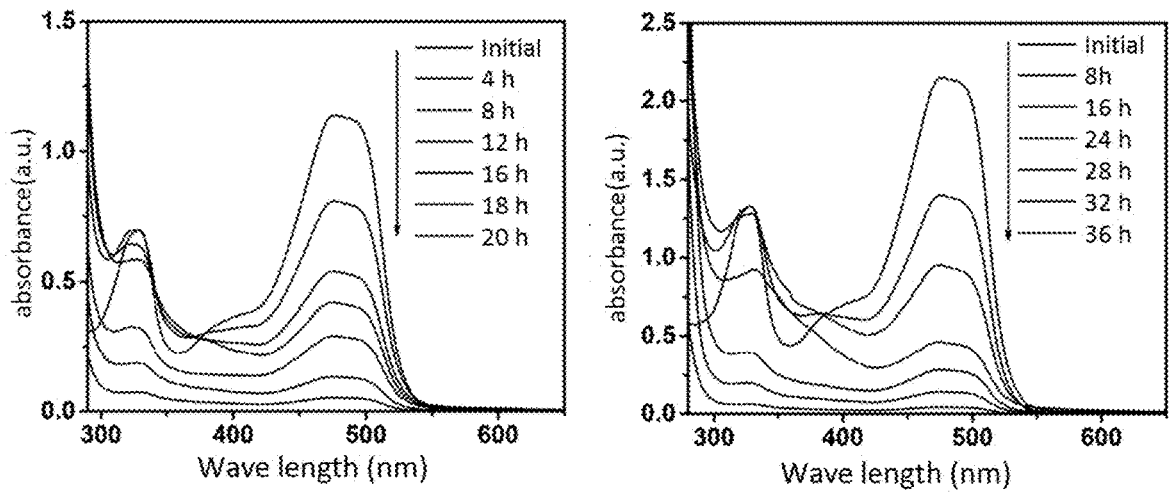
FIG. 6 shows the effect of degradation of free microorganisms.

FIG. 6 is the degradation effect of free microorganisms, it can be seen that acidic oranges, which were initially at 25 mg per liter (left) and 50 mg per liter (right), were degraded over 20 and 36 hours.

Figure 7:
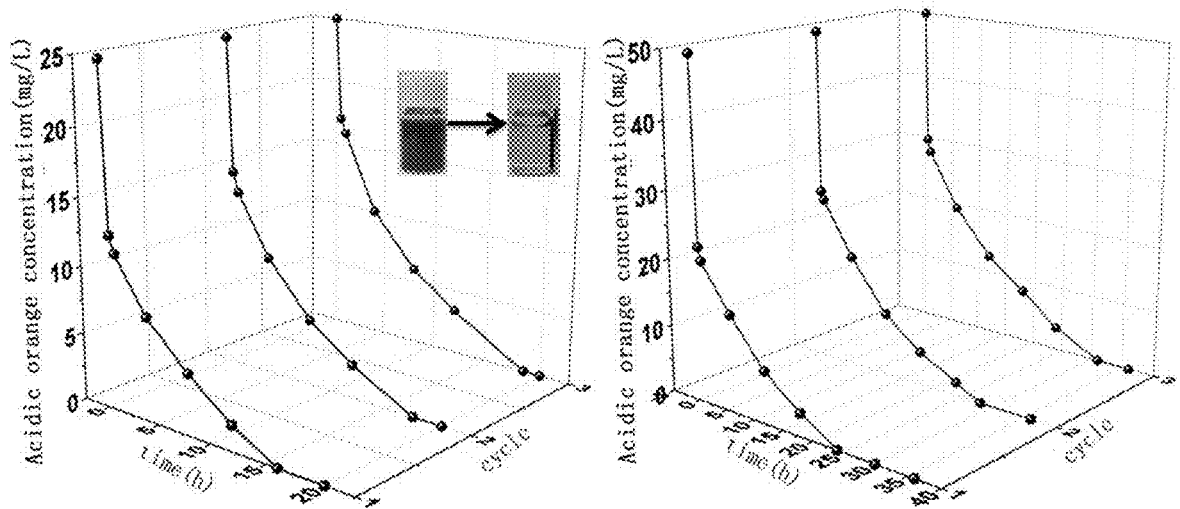
FIG. 7 for the composite material cycle diagram and separation effect.

FIG. 7 shows the cycle performance and the separation effect of the magnetic nano-particle microbe composite with the core-shell structure. It can be seen that the magnetic nano-particle microbe composite has better degradation effect after repeated three times of magnetic separation.

Through the above analysis, the composite disclosed in the present invention shows that the composite material has a strong capability of degrading dyes on microorganisms, has high degradation efficiency, and the production process is simple, convenient, economic and environmental, recyclable, etc., so in waste water treatment it will have a good application.

What is claimed is:

1. A preparation method of magnetic nanoparticle microbial composite material with core-shell structure, characterized in comprising the following steps:
   (1) dissolving a mixture of ferric chloride, sodium citrate, sodium acetate, and ethylene glycol at 180° C. to 200° C. for 8 to 10 hours to prepare ferroferric oxide nanoparticles; then dispersing the ferroferric oxide nanoparticles to an alcohol solution, and then adding thioglycolic acid and ultrasonically reacting to prepare modified ferroferric oxide nanoparticles;
   (2) reacting the modified ferroferric oxide nanoparticles sequentially with ferric chloride and trimesic acid to prepare core-shell structured magnetic nanoparticles; repeating the reaction of the modified ferroferric oxide nanoparticles with ferric chloride and trimesic acid 8 to 20 times;
   (3) modifying the core-shell structured magnetic nanoparticles to a surface of a microbial to prepare the magnetic nanoparticle microbial composite with core-shell structure.

2. The preparation method of magnetic nanoparticle microbial composite material with core-shell structure according to claim 1, wherein in step (1), the mass ratio of ferric chloride, sodium citrate and sodium acetate is 1:(1.5 to 2):10; the mass ratio of ferroferric oxide nanoparticles and thioglycolic acid is 100:(1 to 2); the ultrasonic reaction is carried out at room temperature, ultrasonic reaction time is 6 to 7 hours.

3. The preparation method of magnetic nanoparticle microbial composite material with core-shell structure according to claim 1, wherein in step (2), the reaction time of the modified ferroferric oxide nanoparticle with ferric chloride is half an hour each time, the reaction time with trimesic acid is 1 hour each time.

4. The preparation method of magnetic nanoparticle microbial composite material with core-shell structure according to claim 1, wherein in step (3), the mass ratio of the magnetic nanoparticles to the microorganism is 1:(15 to 20); the core-shell structure of magnetic nanoparticles and microorganisms are reacted in a buffer solution, to achieve modification of the core-shell structure of magnetic nanoparticles to the surface of microorganisms.

5. A preparation method of magnetic nanoparticle microbial composite material with core-shell structure, characterized in comprising the following steps:
   (1) dissolving a mixture of ferric chloride, sodium citrate, sodium acetate, and ethylene glycol at 180° C. to 200° C. for 8 to 10 hours to prepare ferroferric oxide nanoparticles; and then dispersing the ferroferric oxide nanoparticles to an alcohol solution, then adding thioglycolic acid, and ultrasonically reacting to prepare modified ferroferric oxide nanoparticles;
   (2) reacting the modified ferroferric oxide nano particles sequentially with ferric chloride and trimesic acid to prepare magnetic nanoparticles with core-shell structure; repeating the reaction of the modified ferroferric oxide nanoparticles with ferric chloride and trimesic acid 8 to 20 times.

6. The preparation method of magnetic nanoparticle microbial composite material with core-shell structure according to claim 5, wherein in step (1), the mass ratio of ferric chloride, sodium citrate and sodium acetate is 1:(1.5 to 2):10; the mass ratio of ferroferric oxide nanoparticles and thioglycolic acid is 100:(1 to 2); the ultrasonic reaction is carried out at room temperature, ultrasonic reaction time is 6 to 7 hours.

7. The preparation method of magnetic nanoparticle microbial composite material with core-shell structure according to claim 5, wherein in step (2), the reaction time of the modified ferroferric oxide nanoparticle with ferric chloride is half an hour each time, the reaction time with trimesic acid is 1 hour each time.

* * * * *